United States Patent
Shakespeare et al.

(10) Patent No.: US 6,760,103 B2
(45) Date of Patent: Jul. 6, 2004

(54) MEASUREMENT OF PAPER OR BOARD

(75) Inventors: Tarja Shakespeare, Siuro (FI); Petri Soininen, Pirkkala (FI); Jouni Vuorela, Vesilahti (FI)

(73) Assignee: Metso Automation Oy, Helsinki (FI)

(*) Notice: Subject to any disclaimer, the term of this patent is extended or adjusted under 35 U.S.C. 154(b) by 0 days.

(21) Appl. No.: 10/382,455

(22) Filed: Mar. 6, 2003

(65) Prior Publication Data

US 2004/0021869 A1 Feb. 5, 2004

Related U.S. Application Data

(63) Continuation of application No. PCT/FI01/00769, filed on Sep. 5, 2001.

(30) Foreign Application Priority Data

Sep. 6, 2000 (FI) ............................................. 20001970

(51) Int. Cl.[7] ............................. G01J 3/00; G01N 21/89
(52) U.S. Cl. ........................ 356/300; 356/429; 356/432
(58) Field of Search ......................... 356/300, 429–430, 356/432–435

(56) References Cited

U.S. PATENT DOCUMENTS

| | | | |
|---|---|---|---|
| 3,936,189 A | | 2/1976 | De Remigis |
| 4,944,594 A | * | 7/1990 | Burk .......................... 356/429 |
| 5,047,652 A | | 9/1991 | Lisnyansky et al. |
| 5,642,189 A | * | 6/1997 | Alguard ...................... 356/328 |
| 5,793,486 A | | 8/1998 | Gordon et al. |
| 5,822,070 A | * | 10/1998 | Syre .......................... 356/429 |
| 6,498,646 B1 | * | 12/2002 | Typpo et al. ............... 356/429 |

FOREIGN PATENT DOCUMENTS

EP  0 299 194 A3  1/1989

OTHER PUBLICATIONS

Kubelka, Paul, New Contributions to the Optics of Intensely Light–Scattering Materials. Part I; Journal of the Optical Society of America, vol. 38, No. 5, May, 1948, pp. 448–457.

* cited by examiner

*Primary Examiner*—F. L. Evans
*Assistant Examiner*—Kara Geisel
(74) *Attorney, Agent, or Firm*—Alston & Bird LLP

(57) ABSTRACT

The invention relates to a method and arrangement for measuring optical properties from paper or board that constitutes a target to be measured and comprises two planar surfaces. In the arrangement, one surface of the target to be measured is illuminated by an optical power source, and the illuminated area on the opposite side of the illuminated surface comprises at least one backing with known optical properties. A detector detects the illuminated surface in the area of the backing, and at least one optical property of the target to be measured is determined by means of spectral information obtained at the backing.

50 Claims, 5 Drawing Sheets

MEASUREMENT OF PAPER OR BOARD

CROSS-REFERENCE TO RELATED APPLICATIONS

Figure 1A:
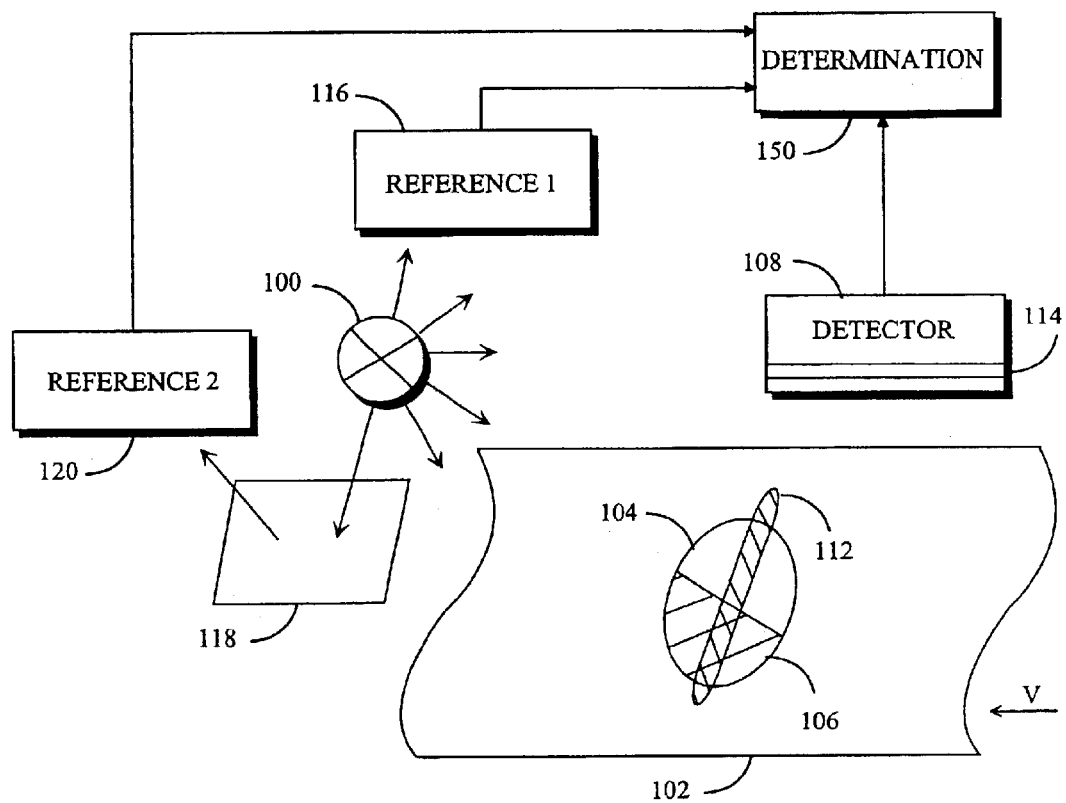

This application is a Continuation of International Application PCT/FI01/00769 filed on Sep. 5, 2001, which designated the U.S. and was published under PCT Article 21(2) in English, and which is hereby incorporated herein in its entirety by reference.

BACKGROUND OF THE INVENTION

1. Field of the Invention

The invention relates to measuring optical properties of paper or board.

2. Description of Related Art

Measuring optical properties of paper or board is a demanding yet important task. Optical properties, such as opacity, color, lightness, brightness, fluorescence etc., are determined by measuring particularly reflectivity but also transmissivity of paper. Measurement of reflectance relates to measuring reflectance factors of a single sheet of paper or a bundle of sheets. Problems occurring during paper measurement result from the partial translucency of paper, which can be eliminated in laboratory measurements by piling up several sheets of the same paper sample, i.e. by forming a stack of paper to be measured. However, this method is not suitable for on-line measurement of a moving paper web. Problems occur particularly in measurements where the same paper property, such as color, is measured by means of on-line and laboratory measurements, which should correspond to one another.

A measurement result corresponding to stack measurement can be obtained by measuring the reflectance of a single paper web or sheet with a suitable backing being arranged behind the paper. The backing can also create an impression of an infinitely thick stack. It is also possible to use two different backings, i.e. a black backing (highly absorptive) and a white backing (highly reflective). When measurement is carried out by means of these two backings, the Kubelka-Munk theory can be utilized to form reflectance factors for a single sheet of paper and an infinitely thick stack of paper.

One manner of determining reflectance factors is to measure the spectrum of the radiation reflected from a black and a white backing. Since nonsimultaneous measurement of different backings would also lead to measurements being carried out on different parts of a moving paper web, the measurements are preferably implemented simultaneously. Measurements are thus performed by means of two spectrometers, one of which measures the radiation reflected from the black backing and the other one measures the radiation reflected from the white backing. Such an arrangement is disclosed in more detail in U.S. Pat. No. 5,793,486, which is incorporated herein by reference. This arrangement enables for example wavelength-specific opacity corrections before color co-ordinate calculation. However, a drawback is the use of two separate spectrometers, which makes the measuring arrangement more complex and increases costs. Furthermore, when two or more detectors are used for measurement, the detectors should be exactly at the same temperature in order to measure in the same manner. The arrangement disclosed in U.S. Pat. No. 5,793,486 is also sensitive to changes in the distance of the paper web.

BRIEF SUMMARY OF THE INVENTION

An object of the present invention is to provide an improved method and an arrangement implementing the method that reduce complexity. This is obtained by a method of measuring optical properties from paper or board that constitutes a target to be measured and comprises two planar surfaces. Further, the method comprises illuminating one surface of the target to be measured, the illuminated area on the opposite side of the illuminated surface comprising at least two backings with different optical properties, detecting the illuminated surface in the area of at least two different backings by means of at least a two-dimensional detecting surface, forming at least two spectra from the areas of at least two different backings of the illuminated surface on at least a two-dimensional detecting surface, and determining at least one optical property of the target to be measured by means of the spectra.

The invention also relates to a method of measuring optical properties from paper or board that constitutes a target to be measured and comprises two planar surfaces. The method further comprises measuring optically the transmittance of the target to be measured, illuminating one surface of the target to be measured, the illuminated area on the opposite side of the illuminated surface comprising at least one backing with known optical properties, detecting the illuminated surface in the area of at least one backing by means of at least a two-dimensional detecting surface, forming at least one spectrum from the area of at least one backing of the illuminated surface on at least a two-dimensional detecting surface, and determining at least one optical property of the target to be measured by means of at least one measured spectrum and measurement of transmittance.

The invention also relates to a method of measuring optical properties from paper or board that constitutes a target to be measured and comprises two planar surfaces. The method further comprises illuminating the target to be measured from one side and forming an image containing spectral information from the opposite side of the target to be measured, illuminating one surface of the target to be measured, the illuminated area on the opposite side of the illuminated surface comprising at least one backing with known optical properties, detecting the illuminated surface in the area of at least one backing on at least a two-dimensional detecting surface, forming at least one image containing spectral information from the area of at least one backing of the illuminated surface on at least a two-dimensional detecting surface, and determining at least one optical property of the target to be measured by means of the image formed in the area of at least one backing, and the spectral information of an image formed by transmittance measurement.

The invention also relates to an arrangement for measuring optical properties from paper or board that constitutes a target to be measured and comprises two planar surfaces. The arrangement further comprises an optical power source for illuminating one surface of the target to be measured, at least two backings with different optical properties, located in the illuminated area on the opposite side of the illuminated surface, detecting means for detecting the illuminated surface in the area of at least two different backings, and for forming a spectrum from the areas of at least two different backings on at least a two-dimensional detecting surface, and determining means for determining at least one optical property of the target to be measured by means of at least two spectra that were formed.

The invention also relates to an arrangement for measuring optical properties from paper or board that constitutes a target to be measured and comprises two planar surfaces. The arrangement is further arranged to measure optically the transmittance of the target to be measured, the arrangement comprising an optical power source for illuminating one surface of the target to be measured, at least one backing with known optical properties, located on the opposite side of the illuminated surface in the illuminated area, detecting means for detecting the illuminated surface in the area of at least one backing and for forming a spectrum from the area of at least one backing on at least a two-dimensional detecting surface, and determining means for determining at least one optical property of the target to be measured by means of at least one formed spectrum and transmittance measurement The invention also relates to an arrangement for measuring optical properties from paper or board that constitutes a target to be measured and comprises two planar surfaces. The arrangement is further arranged to measure optically the transmittance of the target to be measured, the arrangement comprising an optical power source for illuminating one surface of the target to be measured, and detecting means for forming an image containing spectral information from the opposite side of the target to be measured, at least one backing with known optical properties, located on the opposite side of the illuminated surface in the illuminated area, detecting means for detecting the illuminated surface in the area of at least one backing, and for forming at least one image containing spectral information from the area of at least one backing of the illuminated surface on at least a two-dimensional detecting surface of the detecting means, and determining means for determining at least one optical property of the target to be measured by means of an image formed in the area of at least one backing, and an image formed by transmittance measurement.

The preferred embodiments of the invention are disclosed in the dependent claims.

The invention is based on measuring radiation that is reflected from at least two different backings, and on determining desired optical properties on the basis of the measurement. Another possibility is to measure radiation reflected from at least one backing and to determine desired optical properties by means of transmittance measurement.

The method and the arrangement according to the invention provide several advantages. The use of one spectrometer instead of two reduces complexity and the costs of the arrangement, and eliminates problems with temperature between the detectors.

BRIEF DESCRIPTION OF THE SEVERAL VIEWS OF THE DRAWING(S)

Figure 1B:
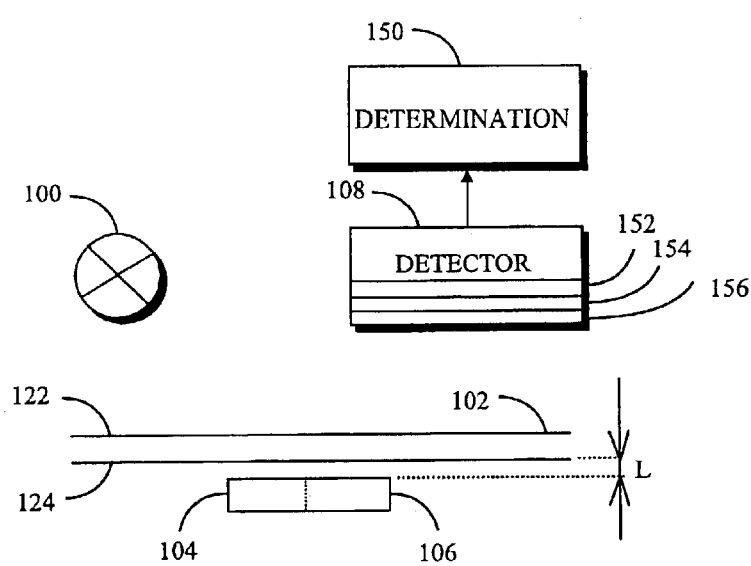
Figure 1C:
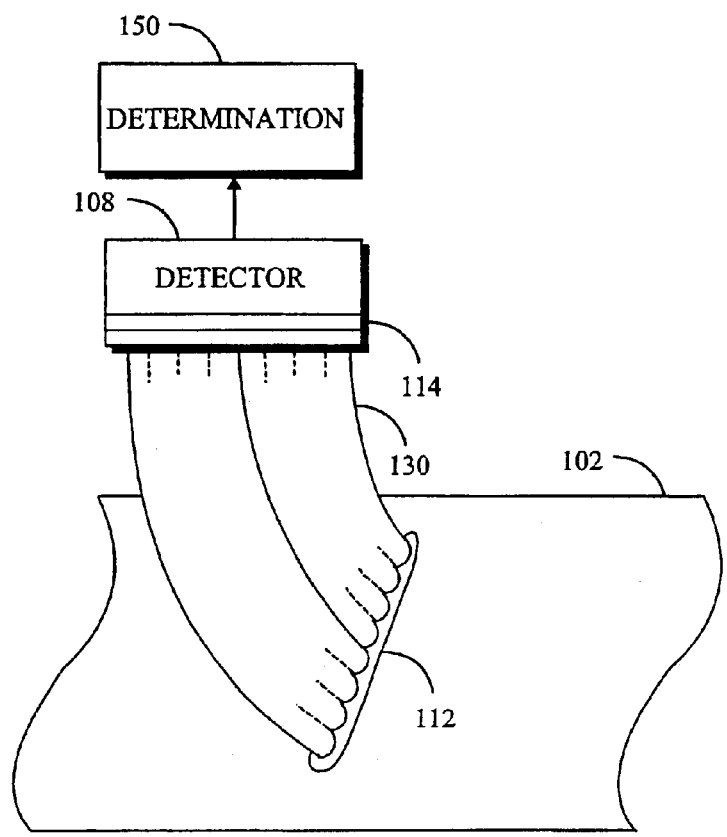
Figure 2A:
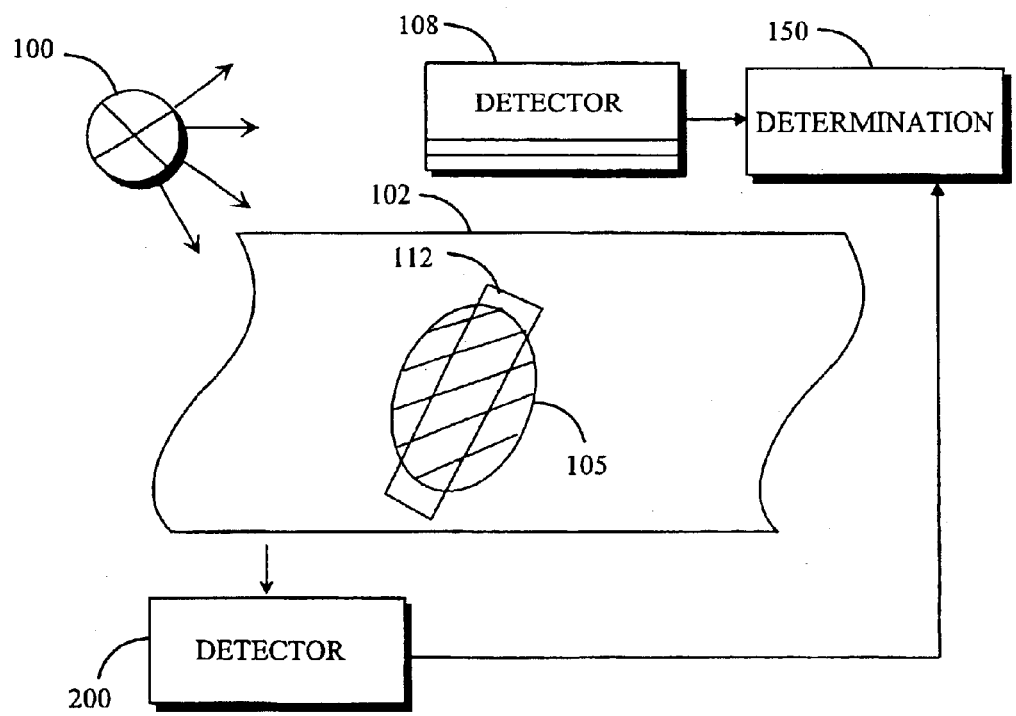
Figure 2B:
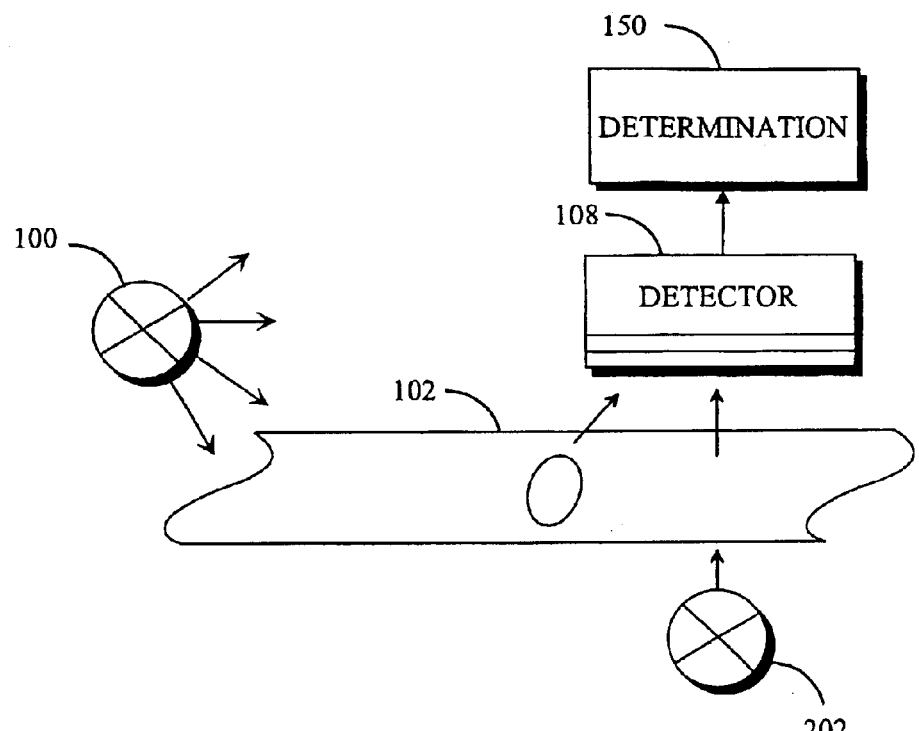
Figure 3:
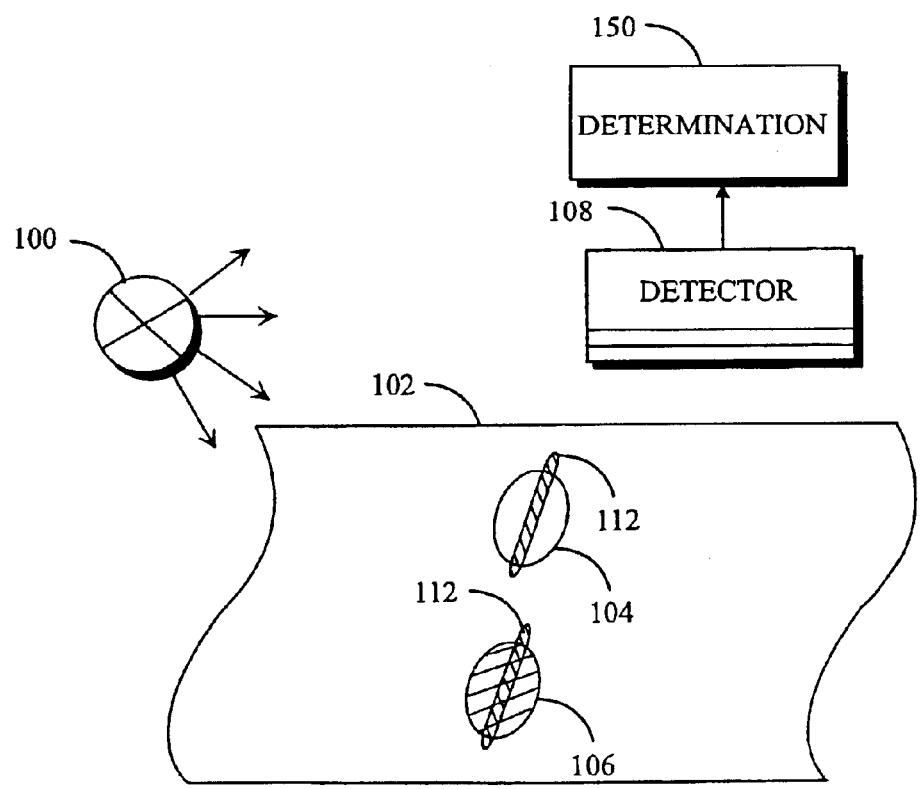
Figure 4:
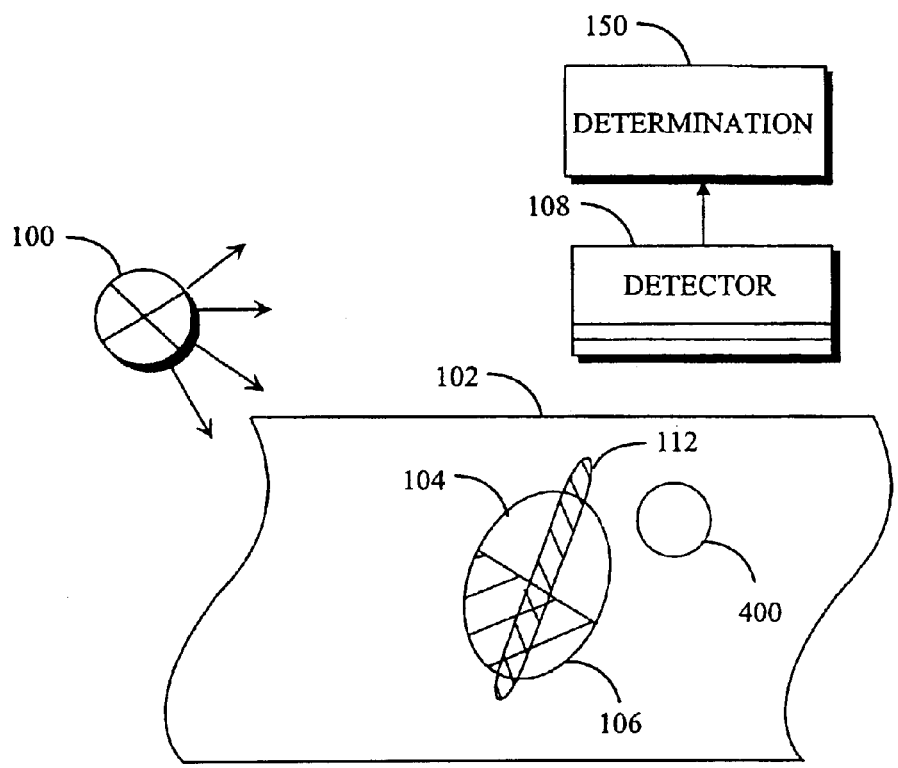
Figure 5:
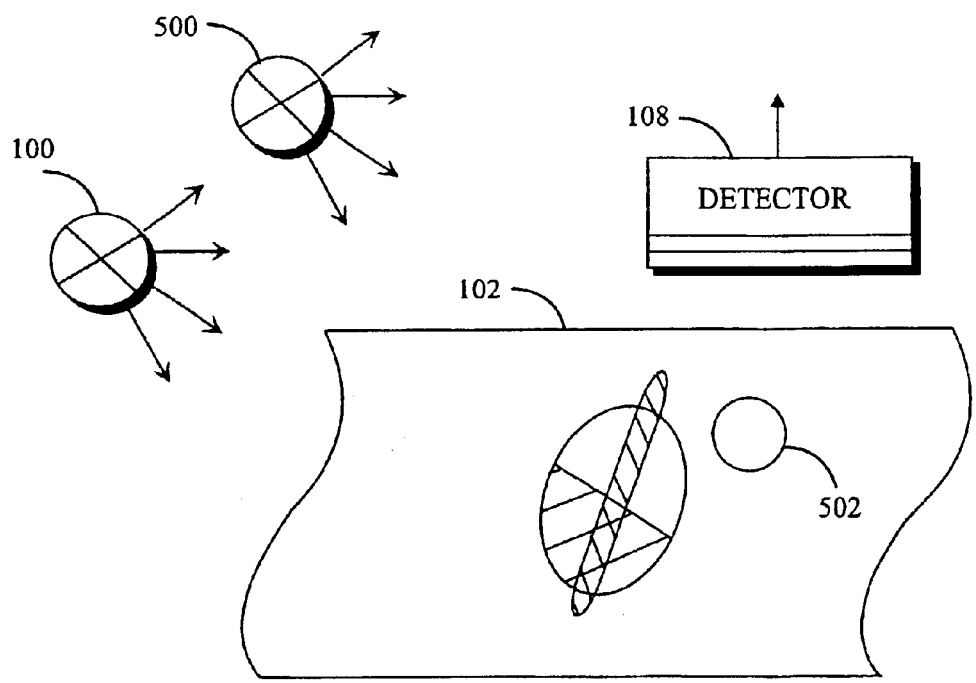
Figure 6A:
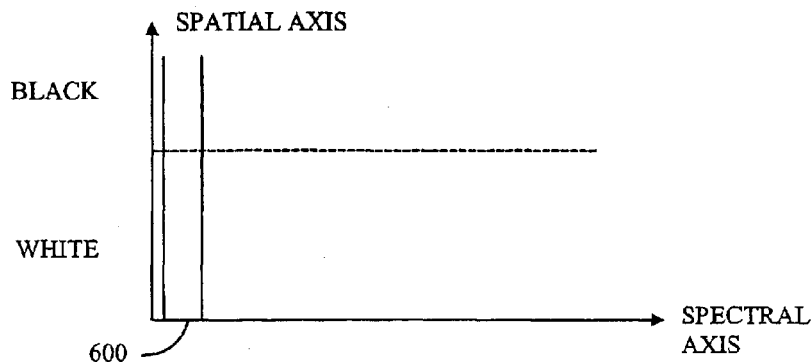
Figure 6B:
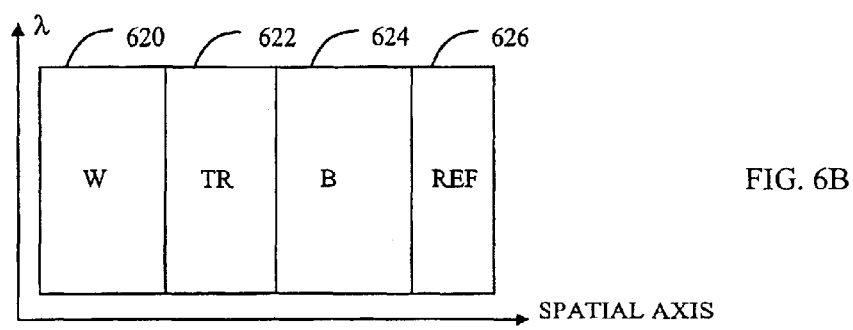
Figure 7:
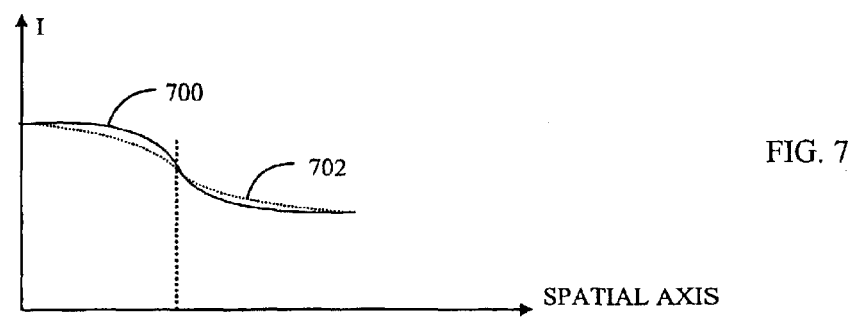
Figure 8:
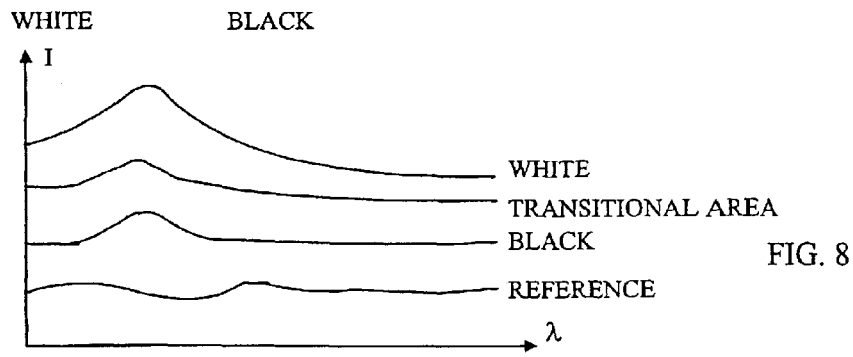

Having thus described the invention in general terms, reference will now be made to the accompanying drawings, which are not necessarily drawn to scale, and wherein:

FIG. 1A shows a measuring arrangement, which measures reflection from two different backings, FIG. 1B is a side view of the measuring arrangement, FIG. 1C shows a measuring arrangement where an optical aperture is implemented by an array of fibers, FIG. 2A shows a measuring arrangement, which measures reflection and transmittance of one backing, FIG. 2B shows a measuring arrangement, which measures reflection and transmittance of one backing, FIG. 3 shows a measuring arrangement where backings are separate, FIG. 4 shows a measuring arrangement utilizing a gray backing, FIG. 5 shows a measuring arrangement for measuring fluorescence, FIG. 6A shows placement of the area to be measured on the spatial and spectral axes of the detector, FIG. 6B shows the division of a detecting surface for different purposes of measurement, FIG. 7 shows an intensity distribution in the transitional area of a white and a black backing, and FIG. 8 shows a spectral intensity distribution.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The arrangement according to the invention is particularly suitable for optical measurements of paper in paper industry, without being restricted thereto, however. The present arrangement can be implemented by a spectrograph, which stores data about the spectral intensity of one or more wavelengths and displays the data graphically. An imaging spectrograph in turn converts dots of a graphical representation (or a spectrum) into digital data, which can be displayed as a visual image, such as a false-color picture. A spectrometer, which is a kind of spectrograph, measures the radiation distribution of a desired wavelength region and displays the spectral data numerically.

Examine first the basic features of the invention by means of FIGS. 1A and 1B. An optical power source 100 emits optical radiation at a target 102 to be measured. The optical power source 100 can be any desired radiator, and it can comprise components, which refract, reflect, scatter and/or filter radiation and provide desired illumination on the surface 102 to be measured. The optical power source 100 comprises one or more radiating elements and it operates either continuously or in a pulsed manner. The optical power source 100 can be either polychromatic or monochromatic. Even though the optical power source 100 is often polychromatic, the target can also be illuminated monochromatically, which means that each monochromatic wavelength band is provided with its own intensity distribution. Radiating elements may consist for example of a number of Light Emitting Diodes (LED). The target 102 to be measured is defined in the present application as paper or board, which is thin, i.e. the thickness of the target to be measured is small compared to its width and length, wherefore the target 102 to be measured comprises mainly two planar surfaces. Measurement can be carried out on an immobile target 102 of measurement, but a usual object of measurement is a paper web moving at speed v and subjected to on-line measurement. In an embodiment of the measuring arrangement, it is essential that one surface 122 of the target 102 to be measured is illuminated either partly or completely, and at the illuminated area on the opposite side 124 of the illuminated surface there are at least two backings 104 and 106 with different optical properties. The backings can be either chromatic or achromatic. An achromatic backing is white, black or gray. A chromatic backing is of some other color than white, black or gray. 'White' means that the backing 104 reflects well (i.e. reflects for example more than 90% of the radiation power directed thereto) the radiation emitted by the optical power source 100 and detected by a detector 108, and 'black' means that the backing 106 absorbs strongly (for example more than 90% of the radiation power directed thereto) the radiation emitted by the optical power source 100 and detected by the detector 108. A light trap also refers herein to a black backing. Different shades of gray in turn reflect a smaller part than a white backing but a greater part than a black backing of the radiation emitted by the optical power source 100 and detected by the detector 108.

When achromatic backings are used, there can be two different backings. In such a case one backing 104 is white and the other backing 106 is black. The detector 108 can comprise at least one dispersing element 114, which can be a grating or a prism. The detector 108 can also comprise an optical aperture and components, which refract, reflect, scatter and/or filter radiation, and which are used to measure a desired pattern from the area 112 of the surface 102 to be measured. The detector 108 detects in at least two dimensions. The detector 108 usually comprises a two-dimensional detecting surface, but three-dimensional detection is also possible. The detector 108 is usually for example a CCD (Charge Coupled Device) camera or the like. Particularly when a broad spectral band is measured, there can be more than one detector 108. In such a case one detector measures for example the infrared (IR) range and the other detector measures the ultraviolet (UV) range.

One alternative of the present arrangement is a multi beam spectrometer, which comprises one common detecting surface. A multi beam spectrometer also comprises at least two slits, which form separate incident rays. The incident rays are scattered into a spectrum by separate dispersing elements into different parts of the detecting surface (e.g. in the longitudinal direction), so that the wavelength axis and the different signals are located in the same dimensional direction of one detector. Another alternative is to use several slits for forming different optical rays but at least one common dispersing element for at least two different optical rays. In such a case, only one dispersing element is normally used to scatter all the rays into a spectrum. An imaging spectrometer comprises several slits for forming different optical signals. Different optical rays are scattered into a spectrum by one dispersing element, and the spectra corresponding to different optical rays are imaged onto different parts of the detecting surface. The wavelength axis is thus located in one dimensional direction of the detector, and the different signals are in a desired order in another dimensional direction of the detector.

The detector 108 can also be sensitive to different wavelengths in depth, so that detection occurs not only on the detecting surface but also in a detecting space, i.e. in three dimensions (shown in FIG. 1B). The detector 108 can comprise for example three layers 152, 154 and 156, such that one layer detects blue, another layer detects green and a third layer detects red. One pixel of the detector 108 can thus measure the intensities of these three colors as spectral information. When a three-dimensional detector is used, a separate dispersing element 114 is not necessarily needed, but the detector detects simultaneously at least two different wavelengths from undispersed radiation. The detector thus detects spatial information (length, width, etc) of the target 102 to be measured in two dimensions and forms the spectral information of the target 102 in the third dimension. The results of the measurement can be used further to form a three-dimensional measuring matrix, which has the wavelength and two spatial directions as axes.

In the present arrangement the area 112 to be measured at the different backings can have any shape and it can form a uniform area, or it can consist of a desired number of separate points to be measured. The area 112 to be measured can be for example a narrow band-like strip, which is detected at least in one dimension by a two-dimensional detecting surface. The dispersing element 114 of the detector 108 forms a spectrum of the area 112 to be measured at least on a two-dimensional detecting surface (e.g. in FIGS. 6A and 6B). The detector 108 obtains an image of the area to be measured via the grating and the input aperture thereof, or, in case of a three-dimensional detector 108, the image of the area to be measured is focused directly on the detector. The area 112 to be measured on the surface of the target to be measured corresponds to the shape of the input aperture of the spectrometer. Therefore the present arrangement enables simultaneous measurement of the reflectance properties at both the black and the white backing.

The radiation power of the optical power source 100 can change in time, and if such a change is not taken into account separately, it is interpreted as a change in the target 102 to be measured. However, a measurement carried out on the target 102 to be measured can be made more accurate by means of reference measurement in all the embodiments of the present arrangement. In such a case a change in the optical power radiated by the optical power source 100 in the illumination of the target 102 to be measured is taken into account either by measuring directly the radiation power of the optical power source 100 by a reference detector 116 or by measuring, by a reference detector 120, the radiation reflected from a known reference surface 118 illuminated by the optical power source 100. The measurement results of the reference measurements and the detector 108 are supplied to determining means 150, which consist of a data processor. The determining means 150 comprise at least one processor for processing data supplied thereto, a memory and required spectral measurement and image processing programs. When two different backings are used, the determining means 150 can form a paper stack estimate for spectral reflectance by means of a spectrum measured from at least two different backings according to the present arrangement.

FIG. 1C shows a manner of implementing an input aperture. An input aperture can be implemented by an array 130 of optical fibers, for example. In such a case, the fiber array 130 is rather close to the target to be measured (usually at most dozens of centimeters from the target to be measured), so that the fibers can view a band-like strip 112 of the surface.

FIG. 2A shows another embodiment of the measuring arrangement. In this arrangement, one surface of the target 102 to be measured is illuminated, and the illuminated area on the opposite side of the illuminated surface comprises at least one backing 105 with known optical properties. The backing 105 can be either achromatic or chromatic. Measurement is otherwise carried out similarly as in the case shown in FIGS. 1A to 1C, but the difference is that the measurement can be carried out by means of only one backing 105. Furthermore, the transmittance properties of the target to be measured are determined such that the radiation transmitted by the optical power source 100 is measured from the opposite side of the target to be measured by a detector 200. It is thus possible to determine desired properties of the target to be measured in a manner known per se. Transmittance and reflectance are preferably measured simultaneously. When a reflectance factor $R_0$ of a single sheet of paper against a black backing is measured together with a transmittance factor T of a single paper sheet, it is possible to determine the reflectivity $R_\infty$ of the paper according to the Kubelka-Munk theory. The reflection $R_\infty$ can be presented in the form $R_\infty = a - b$, where $b = \sqrt{a^2 - 1}$ and $$a = \frac{1 + R_0^2 - T^2}{2R_0}.$$

By providing the expressions for a and b with the values of the reflectance factor $R_0$ and the transmittance factor T, it is possible to calculate the reflectivity $R_\lor$. The Kubelka-Munk theory is discussed in more detail for example in *New contributions of the optics of intensely light-scattering materials*, Part I, by Paul Kubelka, in Journal of the optical society of America, pp 448–457, vol. 38, number 5, May 1948, which is incorporated herein by reference. The reflectance factor $R_0$ and the reflectivity $R_\infty$ can be used to determine for example opacity O as follows:

$$O = 100\% \cdot \frac{\overline{R}_0}{\overline{R}_\infty},$$

wherein $\overline{R}_0$ is the average of the reflectance factor and $\overline{R}_\infty$ is the average of the reflectivity. In the present arrangement, the determining means 150 using measured transmittance and the spectrum measured in the area of at least one backing can also form a paper stack estimate for spectral reflectance, variation of at least one optical property, spectral structure of paper (such as flocculation and formation), paper appearance (such as mottling and orange peel), and an estimate for the spatial homogeneity of paper raw materials or additives. Particularly the use of transmittance measurement for determination of a stack estimate is insensitive to changes in the distance of the paper web.

However, it is not important for the invention how measurement results are processed or what the measurements determine, but the only essential factor is the manner of measurement.

FIG. 2B also shows transmittance measurement. In addition to reflectance measurement, the target 102 to be measured is thus also subjected to optical radiation emitted by an optical power source 202, and the transmittance of the target 102 to be measured is determined by means of the detector 108. Transmittance measurement can also utilize some other detector (not shown in the figure) than detector 108.

In the cases shown in both FIGS. 2A and 2B, it is possible that the detectors 108 and 200 form an image containing spectral information. An image containing spectral information can be formed by means of one or more detectors. When several detectors are used, at least two detectors, which are optimized for different wavelength ranges, detect the target to be measured, and the spectral information the detectors receive is combined into a single image for example in a data processor. The image can be a color image or it can comprise a spectrum of picture elements. In this arrangement the optical power source 100 illuminates one surface 122 of the target 102 to be measured, and the detecting means 200 form an image containing spectral information from the opposite side of the target 102 to be measured. At least one backing 105 with known optical properties is placed on the opposite side of the illuminated surface 112 at the illuminated area. The detecting means 108 detect the illuminated surface at the area 112 of the backing 105 and form for the detecting surface of the detecting means 108 at least one image containing spectral information from the area 112 of the illuminated surface at the backing 105. The determining means 150 determine at least one optical property of the target 102 to be measured by means of transmittance measurement and the image formed at the backing 105. The images that were formed can be used to determine a stack estimate for spectral reflectance, the variation of at least one optical property, the spectral structure of paper, such as flocculation and formation, paper appearance, such as mottling and orange peel, and an estimate for the local variation in adhesion and adsorption of paper additives.

In the arrangement disclosed generally, each pixel in the image formed by the detector can be used to form a separate spectrum, so that it is possible to determine either an average optical property for the entire area of the image, or different deviations of optical properties. The present arrangement can be used to determine uniformity of paper particle distributions, such as flocculation or even spectral formation. In such a case, it is possible to utilize general image-processing methods in addition to spectroscopic methods. In the present arrangement an optical property refers to any result obtained when the electromagnetic radiation used interacts with the target to be measured.

The present arrangement will be further discussed with reference to FIG. 3. In this situation, two different achromatic backings 104 (white) and 106 (black) are not adjacent to one another, but they are clearly separate. There can be even more achromatic backings in the present arrangement. In such a case, also the band-like slit in the detector 108 consists of two parts, such that one part of the slit is located at backing 104 and the other part at backing 106.

FIG. 4 shows an embodiment of the present arrangement, which comprises at least one gray backing 400 in addition to the actual two backings 104 and 106. The detector 108 measures variations in the intensity of backings 104 and 106, as well as backing 400, and the variations are proportional to the distance L between backing 400 and the target 102 to be measured. FIG. 1B illustrates the distance between the backing and the target to be measured. The gray backing 400 can also be located inside either one or each of backings 104 and 106. The gray backing 400 is measured for example by supplying radiation from the area of the gray backing 400 to some part of the detector's 108 input aperture, and by supplying radiation from the area of the actual backings 104 and 106 to the remaining area of the detector's input aperture. Therefore, the radiation supplied from the different backings is distributed over different parts of the detecting surface in the detector.

The present arrangement usually measures opacity. Other properties that can be measured comprise opacity, color, lightness, whiteness, brightness, fluorescence, reflectance factors, total radiance factors, absorption coefficients, scattering coefficients and transmittance. Fluorescence can also be measured. This is shown in FIG. 5. In order to measure fluorescence, the surface of the target 102 to be measured is illuminated by different UV radiation power levels, which can be implemented for example by using, in addition to the optical power source 100 used for the actual illumination of the surface, another optical power source 500, which radiates particularly in the UV range. In such a case, the actual optical power source 100 is not considered to really radiate in the UV range. When the second optical power source 500 is pulsed such that at least some of the individual measurements are carried out only when the actual optical power source 100 illuminates the target and that at least some of the individual measurements are carried out when the second optical power source 500 illuminates either alone or together with the actual optical power source 100, the target to be measured can be measured at different UV radiation intensity levels. The use of two optical power sources also requires two references in order to know the intensities of each optical source. It is thus possible to combine and normalize both measurement results. When two optical power sources are used, the optical paths thereof can also be combined and mixed, so that only one reference can be used. Fluorescence also occurs in visible light, which means that daylight fluorescent materials both excite and emit on the visible light band. The fluorescence of the target 102 to be measured in visible light can be measured by illuminating the target 102 by different visible light power levels similarly as in the measurement of UV fluorescence.

FIGS. 6A and 6B show the use of the detector's detecting surface in measurement of backings and reference. In FIG. 6A, the vertical axis shows the spatial location in the longitudinal direction of a band-like strip 600, and the horizontal axis shows spectral distribution at different wavelengths. The broken line shows the dividing line between a white and a black backing if the backings are adjacent to one another. The spectrometer can also comprise several dispersing elements, which are used to form a spectrum of the band-like strip in the direction of one dimension of the two-dimensional detecting surface. The different dispersing elements are optimized for different wavelength ranges, such as UV radiation, visible light and IR radiation. This provides an efficient and good-quality spectrum over a broad band for example for UV radiation and visible light, or for visible light and IR radiation.

FIG. 6B shows one possible manner of dividing a detecting surface. In this figure the vertical axis shows spectral distribution and the horizontal axis shows spatial distribution. The spectral distribution 620 of the white backing is located on the left side of the detecting surface. This is followed by a transitional area 622 if the black and the white backing have a common dividing line. The next element in the figure is the range of spectral distribution 624 of the black backing. The last is the spectral distribution 626 of reference measurement.

FIG. 7 shows the behavior of intensity in the area of the black and the white backing, when the backings are adjacent to one another. The rate at which the optical power changes depends on the distance L (shown in FIG. 1B) between the backing and the target of measurement. The rate of change of the optical power in the transitional area becomes apparent in the change of the slope of the intensity curve. For example in the measurement denoted by a continuous line 700, the distance L between the backing and the target to be measured has been smaller than in the case denoted by a broken line 702, since the curve 700 is steeper in the transitional area.

FIG. 8 shows the measured intensity distribution as a function of wavelength. The vertical axis shows intensity (or power) on a freely selected scale, and the horizontal axis shows the wavelength. The uppermost curve 800 shows intensity against a white backing. The second curve 802 from the top shows intensity in the middle of a transitional area between a black backing and a white backing. The second curve 804 from below shows intensity against a black backing. The lowermost curve 806 shows intensity of reference measurement. Measurement carried out on the target 102 to be measured can be specified in all the embodiments of the present arrangement by means of reference measurement, which enables compensating for changes in the intensity of the illumination between calibration measurements, thus efficiently reducing for example drift possibly occurring in the measurement and noise related to impulse measurement.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of measuring optical properties from paper or board that constitutes a target to be measured and comprises two planar surfaces, the method comprising:
    illuminating one surface of the target to be measured, the illuminated area on the opposite side of the illuminated surface comprising at least two backings with different optical properties;
    detecting the illuminated surface in the area of at least two different backings by means of at least a two-dimensional detecting surface;
    forming at least two spectra from the areas of at least two different backings of the illuminated surface on at least a two-dimensional detecting surface; and
    determining at least one optical property of the target to be measured by means of the spectra.

2. A method according to claim 1, the method further comprising: using for detection a three-dimensional detector, which detects spatial information of the target to be measured in two dimensions and forms the spectral information of the target to be measured in the third dimension.

3. A method according to claim 1, the method further comprising: forming a stack estimate for spectral reflectance by means of a spectrum measured in the area of at least two different backings.

4. A method according to claim 1, the method further comprising: using at least two different achromatic backings which are adjacent to one another.

5. A method according to claim 1, the method further comprising: measuring the rate of change of optical power when moving from the area of the first backing to the area of the second backing, and reducing the effect of the variation in the distance between the backing and the target to be measured on the measurement of an optical property by taking into account the rate of change of the optical power in the transitional area between the backings.

6. A method according to claim 1, the method further comprising: using a highly reflective backing and a highly absorptive backing, which are adjacent to one another, and by further using at least one other, gray, achromatic backing.

7. A method of measuring optical properties from paper or board that constitutes a target to be measured and comprises two planar surfaces, the method comprising:
    measuring optically the transmittance of the target to be measured;
    illuminating one surface of the target to be measured, the illuminated area on the opposite side of the illuminated surface comprising at least one backing with known optical properties;
    detecting the illuminated surface in the area of at least one backing by means of at least a two-dimensional detecting surface;
    forming at least one spectrum from the area of at least one backing of the illuminated surface on at least a two-dimensional detecting surface; and
    determining at least one optical property of the target to be measured by means of at least one measured spectrum and measurement of transmittance.

8. A method according to claim 1 or 7, the method further comprising: forming, on the detecting surface, an image containing spectral information from each detected area of the illuminated surface.

9. A method according to claim 7, the method further comprising: carrying out both the transmittance measurement of the target to be measured and the detection of the illuminated surface by means of the same detector.

10. A method according to claim 7, the method further comprising: carrying out both the transmittance measurement of the target to be measured and the detection of the illuminated surface by means of different detectors.

11. A method according to claim 7, the method further comprising: forming a stack estimate for spectral reflectance by means of a spectrum measured in the area of at least one backing and transmittance measurement.

12. A method according to claim 1 or 7, the method further comprising: forming a spectrum of the measured area by means of two or more dispersing elements optimized for different wavelength bands.

13. A method of measuring optical properties from paper or board that constitutes a target to be measured and comprises two planar surfaces, the method comprising:
    illuminating the target to be measured from one side and forming an image containing spectral information from the opposite side of the target to be measured;
    illuminating one surface of the target to be measured, the illuminated area on the opposite side of the illuminated surface comprising at least one backing with known optical properties;
    detecting the illuminated surface in the area of at least one backing on at least a two-dimensional detecting surface;
    forming at least one image containing spectral information from the area of at least one backing of the illuminated surface on at least a two-dimensional detecting surface; and
    determining at least one optical property of the target to be measured by means of the image formed in the area of at least one backing, and the spectral information of an image formed by transmittance measurement.

14. A method according to claim 13, the method further comprising: forming a stack estimate for spectral reflectance by means of an image measured in the area of at least one backing and an image formed by transmittance measurement.

15. A method according to claim 13, the method further comprising: forming the variation of at least one optical property by means of an image measured in the area of at least one backing and an image formed by transmittance measurement.

16. A method according to claim 13, the method further comprising: forming the spectral structure of paper by means of an image measured in the area of at least one backing and an image formed by transmittance measurement.

17. A method according to claim 13, the method further comprising: forming the paper appearance by means of an image measured in the area of at least one backing and an image formed by transmittance measurement.

18. A method according to claim 13, the method further comprising: forming an estimate describing the spatial homogeneity of paper raw materials or additives by means of an image measured in the area of at least one backing and an image formed by transmittance measurement.

19. A method according to claim 1, 7 or 13, wherein the optical property to be measured is at least one of the following: opacity, color, lightness, whiteness, brightness, fluorescence, reflectance factors, total radiance factors, absorption coefficients, scattering coefficients, transmittance.

20. A method according to claim 1, 7 or 13, the method further comprising: taking into account a change in the optical power in the illumination of the target to be measured by measuring the optical power source or a known reference surface that is illuminated by the optical power source.

21. A method according to claim 1, 7 or 13, the method further comprising: taking into account a change in the optical power in the illumination of the target to be measured by measuring the optical power source or a known reference surface that is illuminated by the optical power source, and measuring the fluorescence of the target to be measured by illuminating the target at different wavelength bands and power levels of UV radiation or visible light.

22. A method according to claim 1, 7 or 13, the method further comprising: illuminating the target to be measured by means of pulsed optical radiation.

23. A method according to claim 1, 7 or 13, the method further comprising: illuminating the target to be measured by means of temporally continuous optical radiation.

24. A method according to claim 1, 7 or 13, the method further comprising: forming a spectrum of the measured area by means of a detector which detects simultaneously at least two different wavelengths from undispersed radiation.

25. A method according to claim 1, 7 or 13, the method further comprising: carrying out the measurement during a process of manufacturing paper or board in the form of on-line measurement.

26. An arrangement for measuring optical properties from paper or board that constitutes a target to be measured and comprises two planar surfaces, the arrangement comprising:
    an optical power source for illuminating one surface of the target to be measured;
    at least two backings with different optical properties, located in the illuminated area on the opposite side of the illuminated surface;
    detecting means for detecting the illuminated surface in the area of at least two different backings, and for forming a spectrum from the areas of at least two different backings on at least a two-dimensional detecting surface; and
    determining means for determining at least one optical property of the target to be measured by means of at least two spectra that were formed.

27. An arrangement according to claim 26, wherein the detecting means consist of a three-dimensional detector, which is arranged to detect spatial information of the target to be measured in two dimensions and to form the spectral information of the target to be measured in the third dimension.

28. An arrangement according to claim 26, wherein the determining means are arranged to form a stack estimate for spectral reflectance by means of a spectrum measured in the area of at least two different backings.

29. An arrangement according to claim 26, wherein the arrangement comprises at least two different achromatic backings, which are adjacent to one another.

30. An arrangement according to claim 26, wherein the arrangement is arranged to measure the rate of change of the reflected optical power when moving from the area of the first backing to the area of the second backing, and to reduce the effect of the variation in the distance between the backing and the target to be measured on the measurement by taking into account the rate of change of the optical power in the transitional area between the backings.

31. An arrangement according to claim 26, wherein the arrangement comprises a highly reflective backing and a highly absorptive backing, which are adjacent to one another, the arrangement further comprising at least one gray, achromatic backing.

32. An arrangement for measuring optical properties from paper or board that constitutes a target to be measured and comprises two planar surfaces, wherein the arrangement is arranged to measure optically the transmittance of the target to be measured, the arrangement comprising:
   an optical power source for illuminating one surface of the target to be measured;
   at least one backing with known optical properties, located on the opposite side of the illuminated surface in the illuminated area;
   detecting means for detecting the illuminated surface in the area of at least one backing and for forming a spectrum from the area of at least one backing on at least a two-dimensional detecting surface; and
   determining means for determining at least one optical property of the target to be measured by means of at least one formed spectrum and transmittance measurement.

33. An arrangement according to claim 26 or 32, wherein the detecting means are arranged to form an image containing spectral information from each detected area of the illuminated surface.

34. An arrangement according to claim 32, wherein the arrangement comprises an optical power source for transmittance measurement, and the detecting means are arranged to measure the transmittance of the target to be measured.

35. An arrangement according to claim 32, wherein the arrangement comprises detecting means for transmittance measurement for measuring the transmittance of the target to be measured.

36. An arrangement according to claim 32, wherein the determining means are arranged to form a stack estimate for spectral reflectance by means of a spectrum measured in the area of at least one backing, and transmittance measurement.

37. An arrangement for measuring optical properties from paper or board that constitutes a target to be measured and comprises two planar surfaces, wherein the arrangement is arranged to measure optically the transmittance of the target to be measured, the arrangement comprising:
   an optical power source for illuminating one surface of the target to be measured, and detecting means for forming an image containing spectral information from the opposite side of the target to be measured;
   at least one backing with known optical properties, located on the opposite side of the illuminated surface in the illuminated area;
   detecting means for detecting the illuminated surface in the area of at least one backing, and for forming at least one image containing spectral information from the area of at least one backing of the illuminated surface on at least a two-dimensional detecting surface of the detecting means; and
   determining means for determining at least one optical property of the target to be measured by means of an image formed in the area of at least one backing, and an image formed by transmittance measurement.

38. An arrangement according to claim 37, wherein the determining means are arranged to form a stack estimate for spectral reflectance by means of an image measured in the area of at least one backing and an image formed by transmittance measurement.

39. An arrangement according to claim 37, wherein the determining means are arranged to form the variation of at least one optical property by means of an image measured in the area of at least one backing and an image formed by transmittance measurement.

40. An arrangement according to claim 37, wherein the determining means are arranged to form the spectral structure of paper by means of an image measured in the area of at least one backing and an image formed by transmittance measurement.

41. An arrangement according to claim 37, wherein the determining means are arranged to form paper appearance by means of an image measured in the area of at least one backing and an image formed by transmittance measurement.

42. An arrangement according to claim 37, wherein the determining means are arranged to form an estimate describing the spatial homogeneity of paper raw materials or additives by means of an image measured in the area of at least one backing and an image formed by transmittance measurement.

43. An arrangement according to claim 26, 32 or 37, wherein the detecting means are arranged to detect simultaneously at least two different wavelengths from undispersed radiation.

44. An arrangement according to claim 26, 32 or 37, wherein the optical property to be measured is at least one of the following: opacity, color, lightness, whiteness, brightness, fluorescence, reflectance factors, total radiance factors, absorption coefficients, scattering coefficients, transmittance.

45. An arrangement according to claim 26, 32 or 37, wherein the arrangement is arranged to take into account a change in the optical power affecting the illumination of the target to be measured by measuring the optical power source or a known reference surface that is illuminated by the optical power source.

46. An arrangement according to claim 26, 32 or 37, wherein the arrangement is arranged to take into account a change in the optical power in the illumination of the target to be measured by measuring the optical power source or a known reference surface that is illuminated by the optical power source, and the arrangement is arranged to measure the fluorescence of the target to be measured by illuminating the target at different wavelength bands and power levels of UV radiation or visible light.

47. An arrangement according to claim 26, 32 or 37, wherein the arrangement is arranged to illuminate the target to be measured by means of pulsed optical radiation.

48. An arrangement according to claim 26, 32 or 37, wherein the arrangement is arranged to illuminate the target to be measured by means of temporally continuous optical radiation.

49. An arrangement according to claim 26, 32 or 37, wherein the arrangement comprises at least two dispersing elements optimized for different wavelengths and arranged to form a spectrum of a band-like strip in one dimension of a two-dimensional detecting surface.

50. An arrangement according to claim 26, 32 or 37, wherein the arrangement is a part of a process of manufacturing paper or board, and the arrangement is arranged to carry out on-line measurement.

* * * * *